United States Patent [19]
Iki

[11] Patent Number: 5,815,240
[45] Date of Patent: Sep. 29, 1998

[54] OPHTHALMOLOGIC DEVICE HAVING MEANS FOR CLASSIFYING THE PICTURE DATA IN THE FRAME MEMORY INTO THE BRIGHT POINT REGIONS AND THE MASK REGIONS

[75] Inventor: Yoichi Iki, Tokyo-to, Japan

[73] Assignee: Nikon Corporation, Tokyo, Japan

[21] Appl. No.: 838,778

[22] Filed: Apr. 10, 1997

[30] Foreign Application Priority Data

Apr. 11, 1996 [JP] Japan ................................ 8-089324

[51] Int. Cl.⁶ ........................................................ A61B 3/10
[52] U.S. Cl. ............................ 351/212; 351/205; 351/221
[58] Field of Search ...................................... 351/205, 206, 351/211, 212, 221

[56] References Cited

U.S. PATENT DOCUMENTS

| | | | |
|---|---|---|---|
| 4,859,051 | 8/1989 | Fukuma et al. | 351/211 |
| 4,878,750 | 11/1989 | Sekiguchi | 351/212 |
| 4,917,458 | 4/1990 | Matsumura | 351/212 |
| 5,212,507 | 5/1993 | Fujieda et al. | 351/212 |
| 5,214,456 | 5/1993 | Gersten | 351/212 |
| 5,543,887 | 8/1996 | Akashi | 354/410 |
| 5,548,355 | 8/1996 | Iki | 351/212 |

FOREIGN PATENT DOCUMENTS 0 317 768 A1  5/1989  European Pat. Off. .
63-49131  3/1988  Japan .

*Primary Examiner*—Huy Mai

[57] ABSTRACT

An ophthalmologic device measures corneal curvature and ocular refractive power of the eye by imaging the positions of a plurality of bright points which result from plural light rays and by imaging a predetermined pattern of the eye. The ophthalmologic device includes a frame memory to store picture data of the eye which has been imaged by a video camera. The picture data in memory is classified into bright spot regions in which bright spots are present one at a time, a corneal reflected image region in which a reflected image from the cornea of a predetermined pattern is projected into the fundus of the eye, and mask regions in which the bright points and the corneal reflected image are not present. The picture data having a luminosity greater than a predetermined threshold value is stored for later calculation of a centroid of the bright points to measure the corneal curvature of the eye.

20 Claims, 5 Drawing Sheets

OPHTHALMOLOGIC DEVICE HAVING MEANS FOR CLASSIFYING THE PICTURE DATA IN THE FRAME MEMORY INTO THE BRIGHT POINT REGIONS AND THE MASK REGIONS

CROSS-REFERENCE TO RELATED APPLICATIONS

This application is based upon and claims priority of Japanese Patent Application No. 08-089324 filed Apr. 11, 1996, the contents being incorporated herein by reference.

BACKGROUND OF THE INVENTION

The present invention relates to an ophthalmologic device for measuring corneal curvature. More particularly, the present invention relates to an ophthalmologic device which images the positions of bright points which result from plural light rays radiated onto a subject eye.

In ophthalmologic devices which are generally referred to as "autokeratometers," a subject eye is illuminated with light rays. By detecting the light reflected from the cornea of the eye, the positions of bright points, i.e. points illuminated with reflected light, are detected and the corneal curvature of the eye is measured.

In an autokeratometer, the calculation process regarding the image data from the eye generally includes the calculation of bright point positions. During operation, an autokeratometer radiates plural light rays onto a subject eye. Plural bright points which are respectively produced by each light ray provide image data of the eye, which then is stored in a frame memory. By calculating a centroid of the image data corresponding to the bright points as a position of another bright point, the corneal curvature of the eye is measured.

In the autokeratometer, a program executed by a microprocessor (MPU) interfaces with dedicated hardware to determine the positions of the plural bright points. More specifically, a sequence of steps, such as the following steps 1–4, is executed.

Step 1: image data of a subject eye is stored in memory.

Step 2: frame memory is divided into regions in which there is respectively one bright point for each region.

Step 3: for each respective region of memory which was divided in step 2, all image data stored in the region is scanned in sequence, image data of a luminosity greater than a predetermined threshold is detected, and the addresses of the detected image data are stored.

Step 4: a centroid is calculated from the luminosities of the image data stored in step 3 as the position of a bright point.

Dedicated hardware for use with the above autokeratometer has been disclosed in Japanese Laid-Open Patent Publication JP-A-63-49131. According to this prior art example, dedicated hardware stores image data of a subject eye in plural regions of a frame memory. The stored image data has a luminosity greater than a predetermined threshold value and is stored along with an address provided by an MPU. After storage, the MPU calculates a centroid of the stored image data as a position of a bright point.

In the above-mentioned prior art technology, a program is executed by an MPU to calculate the centroid. For each divided plural region, all address data stored in the region is serially scanned and image data having a luminosity greater than a predetermined threshold value is detected. However, this presents a problem in that excessive processing time is taken. Moreover, by using dedicated hardware, construction is difficult and costs become high.

As one solution for the above problems, the inventors have proposed in U.S. Pat. No. 5,548,355 an improved ophthalmologic device to determine the positions of the bright points. This ophthalmologic device measures corneal curvature of a subject eye by radiating plural light rays onto the eye to produce plural bright points and stores corresponding data in memory. The memory is divided into regions and picture data corresponding to the bright points is stored one at a time. After the picture data of the subject eye is stored in frame memory, the picture data is not scanned in sequence to determine the luminosity data. Rather, the luminosity data along with the addresses of the detected picture data are determined during the initial storage of the picture data into frame memory.

However, in the above prior art ophthalmologic devices, the frame memory becomes divided into regions for the respective bright points and the data corresponding to the bright points is compared with a predetermined threshold value prior to storage. However, the eye is radiated by an external light source, i.e. outside the eye, and consequently natural light and other unnecessary light also illuminates the eye. Thus, images from the unnecessary light are reflected from the cornea of the eye and may also be stored in the storage regions.

In the above example, when a calculation process is later performed to determine the positions of the bright points, the position of a corneal reflection from unnecessary light may be found as a position of a bright point. This results because two bright points are present in one region. Thus, when unnecessary light illuminates the subject eye, the problem is that a suitable calculation process is not performed and correct measurement results are not obtained.

Another ophthalmologic device, in addition to the autokeratometer, is the "autorefractometer." The autorefractometer is a device which projects a predetermined pattern onto the fundus of a subject eye and measures the ocular refractive power of the eye by analyzing a reflected image of the projected pattern from the fundus.

In recent years, yet another optical device termed an "autorefkeratometer" has been developed which combines the autokeratometer and the autorefractometer. The autorefkeratometer is an ophthalmologic device which measures both the corneal curvature and the refractive power of the eye. In order to measure the ocular refractive power, a predetermined pattern is projected into the fundus of the eye because the corneal reflected image reflected by the cornea becomes a hindrance. The measurement operator is required to extinguish the light source used for corneal curvature in order to project the predetermined pattern. Thus, when the calculation process is performed to find the position of the centroid bright point, the position of the corneal reflected image of the predetermined pattern is found as the position of the bright point and a correct measurement result is obtained.

However, according to the prior art example, it is virtually impossible to measure ocular refractive power when measuring the corneal curvature of a subject eye. The measurement operator must measure the corneal curvature and the ocular refractive power independently of each other and there is a time difference between the two measurements due to movement of the human eye. Thus, alignment becomes displaced and errors are made in the second measurement result.

BRIEF SUMMARY OF THE INVENTION

It is therefore an object of the present invention to provide an ophthalmologic device which correctly measures corneal curvature of a subject eye.

It is a further object of the present invention to obtain correct measurement results of corneal curvature of a subject eye during illumination by unnecessary light.

It is a further object of the present invention to project a predetermined pattern onto the fundus of a subject eye in order to measure ocular refractive power.

It is still a further object of the present invention to project a predetermined pattern onto the fundus of a subject eye and obtain correct simultaneous measurement of corneal curvature and ocular refractive power.

Objects of the invention are achieved by an ophthalmologic device to determine corneal curvature of an eye by creating a plurality of bright points on the eye from a corresponding plurality of light rays, the ophthalmologic device including: an imaging unit to produce picture data corresponding to the bright points of the eye; a frame memory to store the picture data produced by the imaging unit; a memory controller to classify the frame memory into bright point regions in which bright points exist one at a time and mask regions in which bright points do not exist; and a control unit to calculate corneal curvature of the eye from the image data stored in the bright point regions of the frame memory.

Further objects of the invention are achieved by an ophthalmologic device to determine corneal curvature of an eye by creating a plurality of bright points on the eye from a corresponding plurality of light rays, the ophthalmologic device including: a light source to project a predetermined pattern onto the eye and thereby produce a corresponding reflected image of the predetermined pattern; an imaging unit to produce picture data including data corresponding to the bright points of the eye and data corresponding to the reflected image; a frame memory to store the picture data produced by the imaging unit; a memory controller to classify the frame memory into bright point regions, a corneal reflected image region and mask regions; and a control unit to determine corneal curvature of the eye from the picture data stored in the bright point regions of the frame memory and to determine ocular refractive power of the eye from the picture data stored in the corneal reflected image region of the frame memory.

Even further objects of the invention are achieved by an ophthalmologic device, including: a first light source to create a plurality of bright points on the eye from a corresponding plurality of light rays; a second light source to project a predetermined pattern onto the eye and thereby produce a corresponding reflected image of the predetermined pattern; an imaging unit to produce picture data including data corresponding to the bright points of the eye and data corresponding to the reflected image; a frame memory to store the picture data produced by the imaging unit; a memory controller to classify the frame memory into bright point regions, a corneal reflected image region and mask regions; a magnitude comparator to compare the picture data stored in the frame memory with a predetermined threshold value; an area memory to store the picture data compared by the magnitude comparator which exceeds the threshold value and which is stored in frame memory in the bright point regions or stored in the corneal reflected image region; and a control unit to determine corneal curvature of the eye and ocular refractive power of the eye from the picture data stored in the frame memory.

BRIEF DESCRIPTION OF THE DRAWINGS

These and other objects and advantages of the invention will become apparent and more readily appreciated from the following description of the preferred embodiments, taken in conjunction with the accompanying drawings of which.

DETAILED DESCRIPTION OF THE PREFERRED EMBODIMENTS

Figure 1:
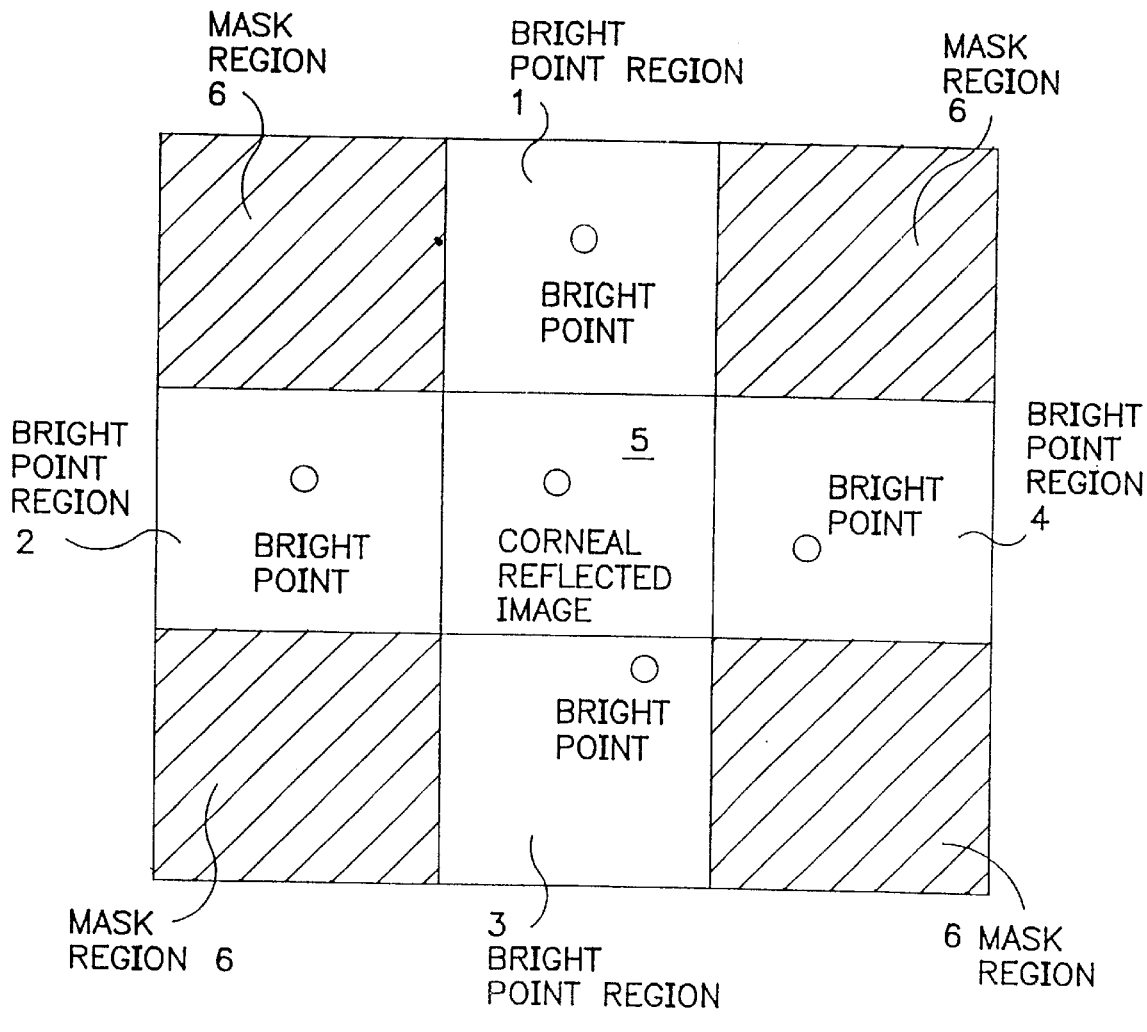
FIG. 1 is a schematic diagram of a frame memory of an ophthalmologic device according to a preferred embodiment of the present invention.

Reference will now be made in detail to the preferred embodiments of the present invention, examples of which are illustrated in the accompanying drawings, wherein like reference numerals refer to like elements throughout.

As set forth below with reference to the accompanying drawings, an ophthalmologic device performs measurements of corneal curvature and ocular refractive power of a subject eye. First, a description is given of an optical system for measuring features of a subject eye. The optical system is illustrated in FIG. 5.

Figure 5:
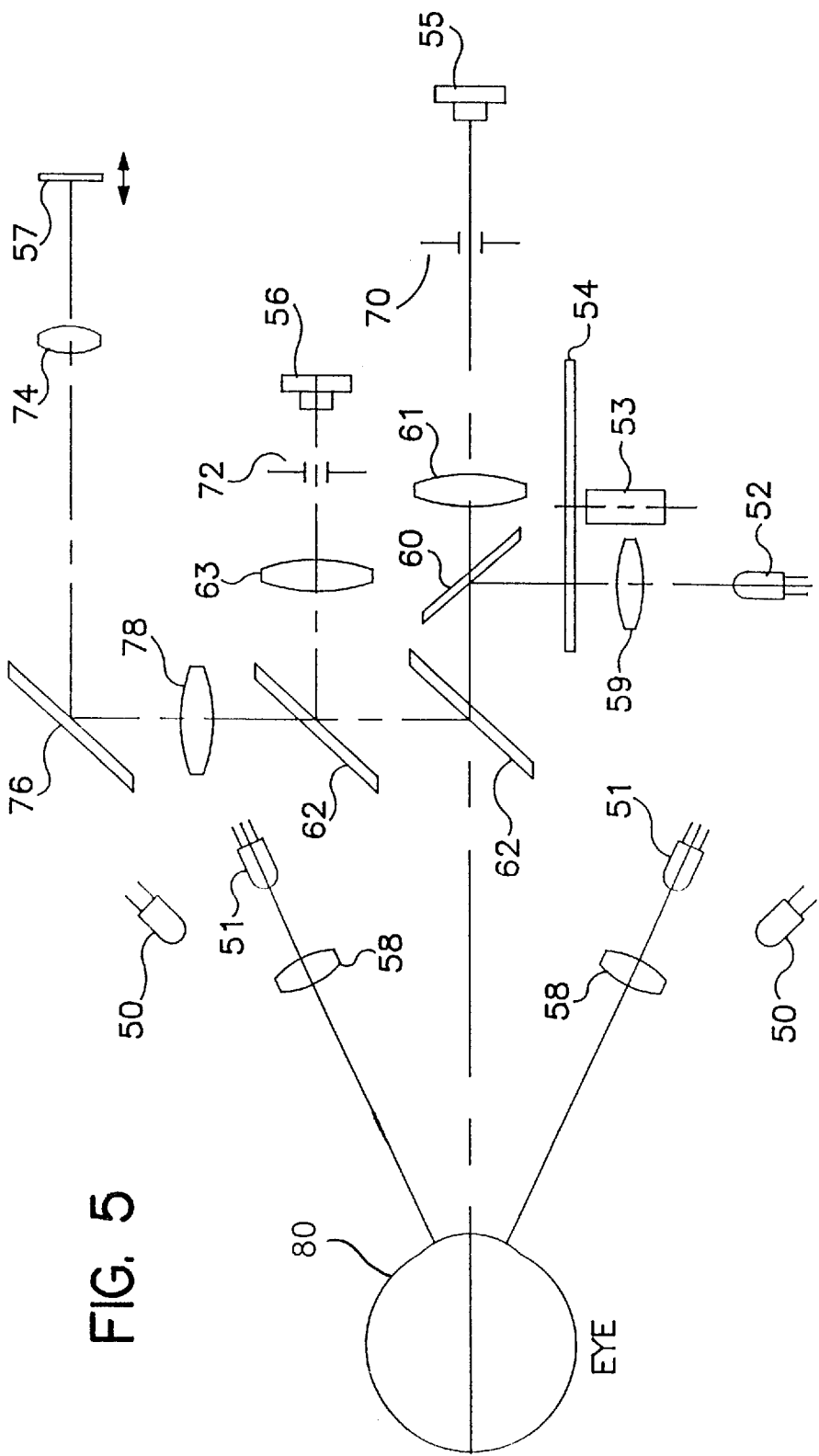
FIG. 5 is a plan view of an optical system of an ophthalmologic device according to a preferred embodiment of the present invention.

With reference to FIG. 5, four light sources 51 (only two are illustrated) are used during corneal curvature measurement to radiate four light rays onto a subject eye 80. The four light sources 51 are located in up and down positions as well as left and right positions with respect to the eye 80. The illustrated light sources 51 are in the left and right positions with two light sources 51 (not shown) in the up and down positions.

One light source 52 is used for ocular refractive power measurement to project a predetermined pattern into the fundus of the subject eye 80. In actuality, the light rays radiated by the light source 52 for use in ocular refractive power measurement have a predetermined pattern which is produced by passing light through a chopper 54 driven by motor 53. However, as set forth below, a light source for use in ocular refractive power measurement will be deemed to include chopper 54.

The light rays radiated by light sources 51 for corneal curvature measurement respectively pass through collimator lenses 58 to reach the cornea of eye 80. On the other hand, the predetermined pattern projected by light source 52 for use in ocular refractive power measurement reaches the fundus of the eye 80 via condenser lens 59 and semi-reflective mirror 60.

The pattern image formed on the fundus of the eye 80 by the predetermined pattern, which is projected by light source 52 for ocular refractive power measurement, reaches the light receiving element 55 via a first semi-reflective mirror 62, semi-reflective mirror 60, objective lens 61, and stop 70. It is then possible to calculate the ocular refractive power from the pattern image received by light receiving element 55.

Bright points arising on the cornea of the eye 80, due to the light rays from light source 51, reach imaging element 56 which is preferably in the form of a video camera. To reach imaging element 56, the bright points from the eye 80 are first reflected by semi-reflective mirrors 62. The light then travels through object lens 63 and stop 72 before being received by imaging element 56. Corneal curvature is then calculated from picture data of the eye 80 which has been imaged by imaging element 56.

In FIG. 5, a fixed visual target 57 fixes the viewing point along a line of sight of the eye and thereby increases accuracy of the measurement results. The line of sight of the eye travels from eye 80, is reflected by a first semi-reflective mirror 62, passes through a second semi-reflective mirror 62, and then passes through objective lens 78. The line of sight of the eye is then reflected by mirror 76 and passes through lens 74 to reach fixed visual target 57. The line of sight of the eye is also reflected by the second semi-reflective mirror 62, passes through objective lens 63 and stop 72 before being received by imaging element 56. Moreover, the line of sight of the eye also travels through the second semi-reflective mirror 62, semi-reflective mirror 60, objective lens 61, stop 70, and is then received by light receiving element 55.

A light source 50 for external illumination outside of the eye 80 also radiates light into the eye. Observation of the eye, i.e. picture data of the eye imaged by the video camera 56 including reflected light from light source 50, is then displayed on a monitor (not shown).

The measuring optical system illustrated in FIG. 5 is somewhat similar to the ophthalmologic device which is termed an "autorefkeratometer". However, more detailed features of the ophthalmologic device according to a preferred embodiment of the present invention are described hereinbelow.

FIG. 1 is a schematic diagram illustrating a frame memory 10 which stores picture data and is classified into three types of regions: bright point regions, a corneal reflected image region, and mask regions. The three regions record data of a subject eye for each image frame from imaging element 56.

In FIG. 1, bright point regions 1–4 are regions in which there are present, one at a time, bright points which arise due to the respective plural light rays which are radiated to the eye from the light source 51 for corneal curvature measurement. Corneal reflected image region 5 is a region in which an image is reflected from the cornea of the eye. The image is a predetermined pattern projected onto the eye from light source 52 for use in ocular refractive power measurement. The mask regions 6 are regions in which the bright points and the cornea reflection image are not present.

Moreover, according to a preferred embodiment of the present invention as illustrated in FIG. 1, four light sources 51 for corneal curvature measurement radiate four light rays onto the eye and are classified into four bright point regions 1–4. Picture data of the eye stored in the corneal reflected image region 5 and the picture data of the eye stored in the mask regions 6 are not processed in order to find the positions of the bright points.

Bright point regions 1–4 are defined from an arbitrary shape of the cornea of the eye and the position of light source 51. The corneal reflected image region 5 is also defined from an arbitrary shape of the cornea of the eye and the position of a light source for use in ocular refractive power measurement. The mask regions 6 can be defined as all remaining regions other than regions 1–4 and 5.

Figure 2:
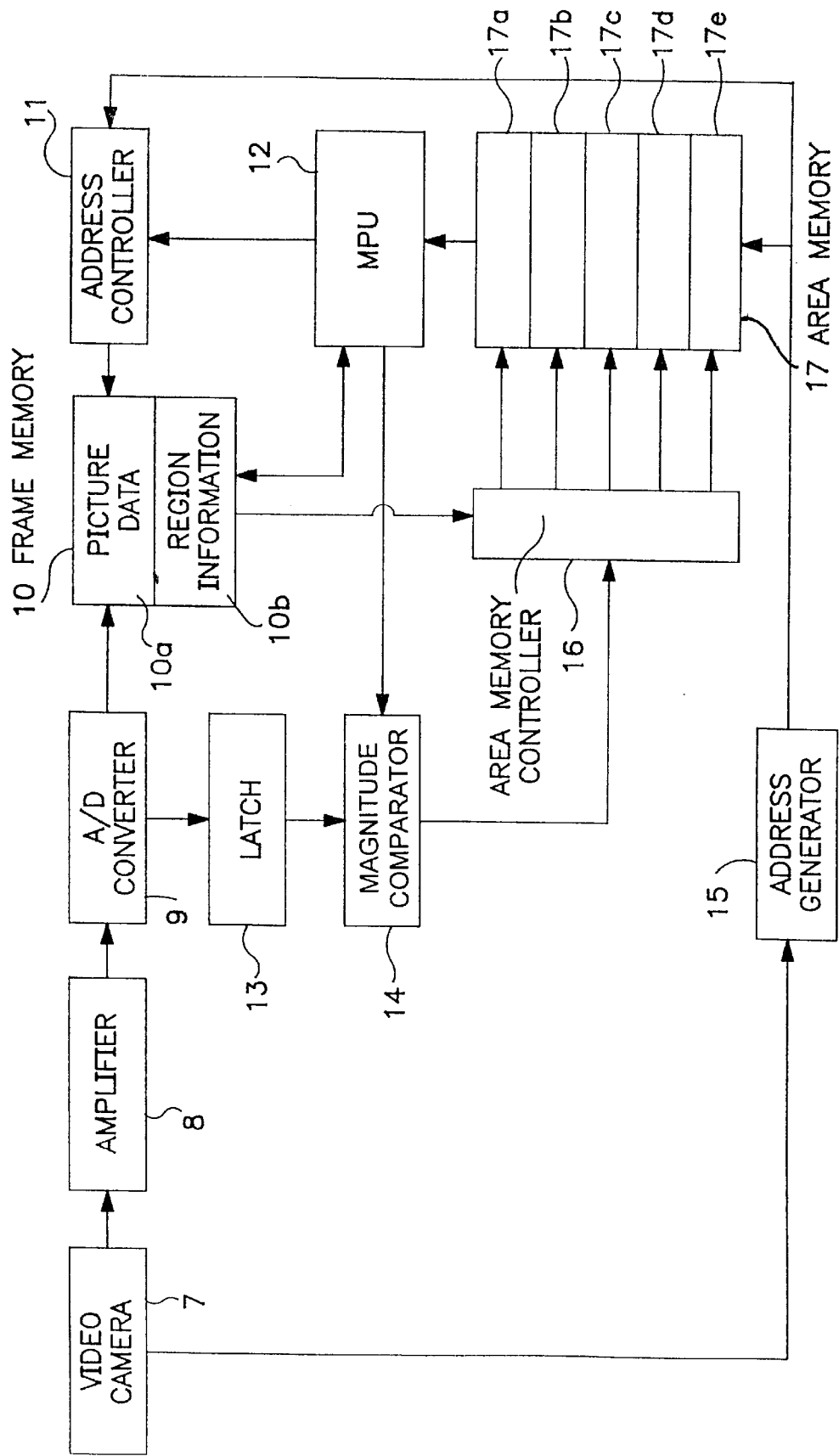
FIG. 2 is a block diagram of a bright point position calculating unit of an ophthalmologic device according to a preferred embodiment of the present invention.

FIG. 2 is a block diagram illustrating a bright point position calculating unit 90 which determines the positions of the bright points in an ophthalmologic device according to a preferred embodiment of the present invention. Bright point position calculating unit 90 is equipped with a video camera 7, an amplifier 8, an A/D converter 9, a frame memory 10, an address controller 11, an MPU 12, a latch 13, a magnitude comparator 14, an address generator 15, an area memory controller 16, and an area memory 17.

The operation of bright point position calculating unit 90 is described below for a case in which the corneal curvature and the ocular refractive power of the eye are measured simultaneously. In the case of simultaneously measuring the corneal curvature and the ocular refractive power of the eye, four light rays are radiated onto the eye from light source 51 for use in corneal curvature measurement. A predetermined pattern is then projected into the fundus of the eye from light source 52.

Consequently, on the cornea of the eye, in addition to the bright points arising from the respective four light rays which are radiated onto the eye from light source 51, a reflected image becomes present from the predetermined pattern which is projected into the fundus of the eye from light source 52.

Thus, in the bright point position calculating unit 90, the eye is imaged by video camera 7, a picture signal of the imaged subject eye is output to amplifier 8, and simultaneously a signal is output to address generator 15. The picture signal input to amplifier 8 is then amplified or attenuated as required and is input to A/D converter 9. The picture signal is digitized at intervals by A/D converter 9 and is indexed by address controller 11. The picture signal is then stored in frame memory 10 by being written into an address of frame memory 10.

The address indexed by address controller 11 is formed by address generator 15. The address generator 15 forms an address of the frame memory for storing the picture data and outputs the formed address to the address controller 11 every time it receives a synchronous signal from video camera 7. Moreover, address generator 15 outputs the formed address to area memory 17.

MPU 12 outputs to address controller 11 the address of the picture data to be read in a case of reading optional picture data stored in frame memory 10. In the case of writing optional picture data into frame memory 10, the address of the data to be written may be output to address controller 11.

On the other hand, the picture data which has been digitized by A/D converter 9 is held by latch 13 and is then input to magnitude comparator 14. This picture data, by way of magnitude comparator 14, is compared with a predetermined threshold value output from MPU 12 to determine whether or not the luminosity is greater than the predetermined threshold value. As a result of this comparison, and in case the luminosity of the picture data is greater than the predetermined threshold value, the address of the picture data is stored in area memory 17 by area memory controller 16.

Figure 3:
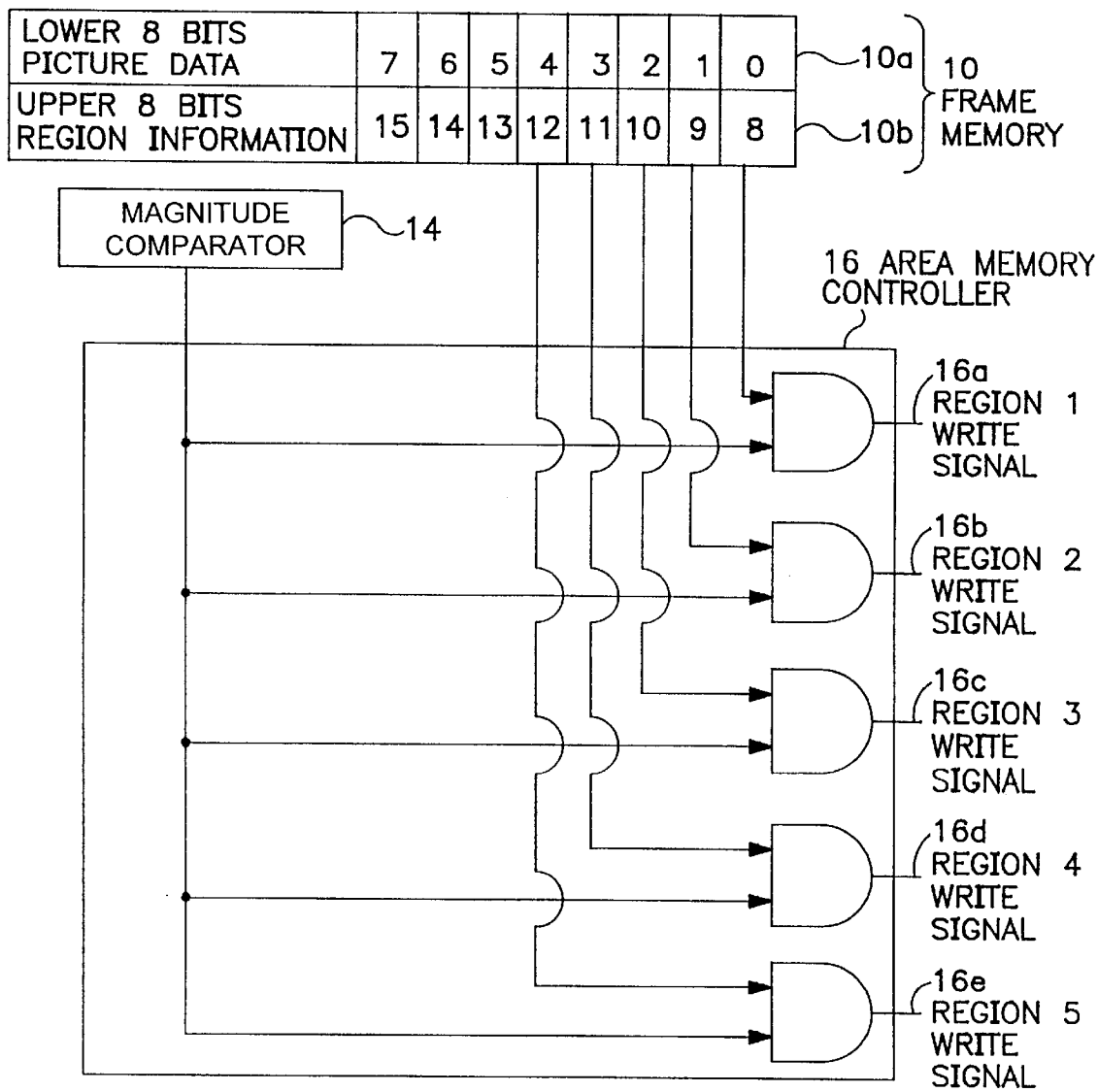
FIG. 3 is a schematic diagram of a frame memory and an area memory controller of an ophthalmologic device according to a preferred embodiment of the present invention.

FIG. 3 illustrates area memory controller 16 and frame memory 10 of FIG. 2. As illustrated, the picture data 10a, which has been digitized by A/D converter 9, is written into frame memory 10. In addition, in the case that the picture data 10a is written into a bright point region 1–4 or cornea reflection image region 5, digitized data is also written into the region information 10b which illustrates the appropriate region.

For example, as illustrated in FIG. 3, in a case that a suitable area in each address of frame memory 10 is 16 bits, the picture data 10a is written into the lower 8 bits (bit 0–bit 7) and the region information 10b is written into the upper 8 bits (bit 8–bit 15).

Moreover, in the example of FIG. 3, among the region information 10b written into the upper 8 bits, bits 13–15 are undefined so as to be interchangeable. Then, by making bits 8–12 correspond to the bright point regions 1–4 and the corneal reflected image region 5, bits 8–12 illustrate the region in which the corresponding picture data is written.

Namely, if bit 8 is "1", data is written in bright point region 1; if bit 9 is "1", data is written in bright point region 2; if bit 10 is "1", data is written bright point region 3; if bit 11 is "1", data is written in bright point region 4; if bit 12 is "1", data is written in cornea reflected image region 5. If bits 8–15 are all "0", then data must be written in mask region 6.

Moreover, an initialization is previously written into the region information 10b by MPU 12 which actualizes the classification mentioned above. The initialization is performed before the calculation of the positions of the bright points. Namely, MPU 12 initializes region information 10b such that this region reflects bright point regions 1–4, corneal reflected image region 5, or mask regions 6, by setting a "0" or a "1" in bits 8–12. Through the operation of MPU 12 initializing the region information 10b, bright point regions 1–4, corneal reflected image region 5, and mask regions 6 may be optionally classified without limitation to the example illustrated in FIG. 1.

When the corresponding picture data 10a is written, region information 10b is read by area memory controller 16. The region information 10b is read by area memory controller 16 and output to a corresponding region in area memory 17. Picture data 10a is then determined to be greater than a predetermined threshold value through a logical sum (AND) with predetermined output signals from MPU 12. Thus, it is possible to determine if a particular region of picture data 10a is greater than a threshold value in hardware.

Through operation of area memory controller 16 when the region information 10b is read out, for example in the case that bit 8 is a value "1", the bits 9–12 are values "0" to show that the region in which the corresponding picture data 10a is written is the bright point region 1. If a signal is output from magnitude comparator 14 indicating that the signal is greater than a threshold value, a write signal 16a corresponding to the bright point region 1 is output to area memory 17.

Moreover, through operation of the area memory controller 16, the region information 10b may be read out in the case that bits 8–11 have values "0" and the bit 12 has a value "1". This shows that the region in which the corresponding picture data 10a is written is a corneal reflected image region 5. If a signal is output from the magnitude comparator 14 indicating that the signal is greater than a threshold signal, a write signal corresponding to the corneal reflected image region 5 is output to area memory 17.

Moreover, through operation of area memory controller 16, the region information 10b may be read out for example in the case that bits 8–12 are "0" such that the region in which the corresponding picture data 10a is written is neither a bright point region 1–4 nor a corneal reflected image region 5. Thus, even if a signal is output from the magnitude comparator 14 indicating that the signal is greater than a threshold value, no write signals 16a–16e are output to area memory 17. This is because the region information indicates a mask region 6.

On the other hand, in the above manner, because an address is always output from address generator 15 for each region, the write signals 16a–16e control the output from area memory controller 16 such that only regions 1–4 and 5 are written into areas 17a–17e. The areas 17a–17e each store one address and writing of a new address overwrites a previously written address.

At a point in time in which the writing of the picture data of the subject eye into the frame memory has ended, the respective corresponding bright point regions 1–4 and corneal reflected image 5 have been written into areas 17a–17e of area memory 17. However, only the picture data 10a having a greater luminosity than a predetermined threshold value is finally stored.

After this, MPU 12 reads out the addresses stored in areas 17a–17d (areas corresponding to the bright point regions 1–4), and calculates as the position of a bright point, the centroid of the luminosities for picture data 10a stored for addresses which were read out.

Here, a method of calculating a centroid of the luminosities, for simplicity, will be described as an example for bright point region 1. In actuality, within the bright point region 1, to find the center of the positions of the bright points, for a range corresponding to the theoretical values of the magnitude of the bright point (this is defined by a light ray radiated by light source 52), the plural picture data 10a which has been written within this range becomes picture data 10a having a luminosity greater than a predetermined threshold value. Further as set forth above, the value of the bright point region 1 is written into the address stored in area memory 17a, and among the picture data 10a having a luminosity greater than the predetermined threshold value, the address of the picture data 10a is written.

Consequently, the MPU 12 calculates the centroid of the luminosities for the address(es) stored in the area memory 17a in a set neighborhood based on theoretical values of the magnitude of the luminosity. For example, the addresses stored in area memory 17a are $(X_n, Y_m)$ in the case that the theoretical values of the magnitudes of the bright points are the maximum values in the X-axis direction and the Y-axis direction $X_{max}$ and $Y_{max}$. The MPU 12 then calculates the centroid $(X_0, Y_0)$ of the luminosities from Equation 1 below:

$$X_0 = \frac{\sum_i X_i \cdot P_{ij}}{\sum_i P_{ij}}$$

$$Y_0 = \frac{\sum_i Y_i \cdot P_{ij}}{\sum_i P_{ij}}$$

Equation 1

The centroid represents picture data which exceeds a predetermined noise level among picture data 10a inside a square region having vertices $(X_n-X_{max}, Y_m-Y_{max})$ and $(X_n+X_{max}, Y_m+Y_{max})$. In Equation 1, $(X_i, Y_i)$ are the addresses of picture data 10a exceeding the noise level, and $P_{ij}$ is the luminosity of the picture data stored in the address $(X_i, Y_j)$. Here $X_i$, $Y_j$ are respective integers such that $(X_n-X_{max}) \leq X_i \leq (X_n+X_{max})$ and $(Y_m-Y_{max}) \leq Y_m \leq (Y_m+Y_{max})$. For more details of the method of calculating the centroid of the luminosities, see Japanese Patent Publication JP-A-6-142045.

When the luminosity is greater than a predetermined threshold value for the picture data 10a written into corneal reflected image region 5, there exists on the cornea of the eye a reflected image of a predetermined pattern projected onto the fundus of the eye by light source 52 for use in ocular refractive power measurement.

However, through operation of an ophthalmologic device according to a preferred embodiment of the present invention, the picture data 10a written into the corneal reflected image region 5 is also of a luminosity greater than a predetermined threshold value. Because the address in which this picture data 10a has been written is stored in area 17e of area memory 17, this picture data can be separated from the calculation to determine the positions of the bright points.

Accordingly, in a case in which light source 52 for ocular refractive power measurement projects a predetermined pattern onto the fundus of the eye, even in a case in which the measurements of the corneal curvature and the ocular refractive power of the eye are simultaneously performed, there are no adverse effects on the calculation process in order to find the position of the bright points and correct measurement results can be obtained.

MPU 12 reads out the addresses which are stored in area 17e of area memory 17 (an area corresponding to the corneal reflected image region 5), and calculates a centroid of the luminosities of the picture data 10a stored in the addresses which were read as a position of the corneal reflected image. Furthermore, by performing an alignment of the eye using this position of the corneal reflected image, from a relative distance of the four bright points which were found, a curvature can be measured which is the average, up and down, and left and right, of the corneal curvature.

Moreover, when image data 10a having a luminosity of bright points greater than a predetermined threshold value is written into the mask regions 6, after the calculation process to determine the positions of the bright points, it is determined that reflected images of unnecessary light exist on the cornea of the eye. However, through operation of an ophthalmologic device according to a preferred embodiment of the present invention, even if the picture data 10a written into the mask regions 6 has luminosities which are greater than a predetermined threshold value, because the address of this written in picture data 10a is not stored in the area memory 17, this information is separated from the calculation process when finding the positions of the bright points.

Light is radiated from a light source 50 as illustrated in FIG. 5 for illumination outside of the subject eye 80. Even in the case when unnecessary light illuminates the eye in the calculation process to find the position of the bright points, the image of the unnecessary light is reflected from the cornea of the eye and is, as far as possible, present in the mask regions 6. However, the unnecessary light does not affect the calculation process which finds the positions of the bright points, and it thus becomes possible to obtain correct measurement results.

Moreover, in an ophthalmologic device according to a preferred embodiment of the present invention, the address of the initially written picture data 10a is stored for picture data 10a having a luminosity greater than a predetermined threshold value. The initially written picture data is written into the bright point regions 1–4 and cornea reflection region 5, which respectively correspond to the areas 17a–17e of area memory 17.

Moreover, in an ophthalmologic device according to a preferred embodiment of the present invention, area memory controller 16 may determine through software a region from which picture data 10a was read based on the region information 10b and a signal output from magnitude comparator 14 in a case that picture data 10a is greater than a predetermined threshold value.

Moreover, in a preferred embodiment of an ophthalmologic device according to the present invention, magnitude comparator 14 compares whether picture data 10a has a luminosity greater than a predetermined threshold value only in a case that area memory controller 16 determines that some bright point regions 1–4 and the corneal reflected image region 5 have been written into picture data 10a.

Figure 4:
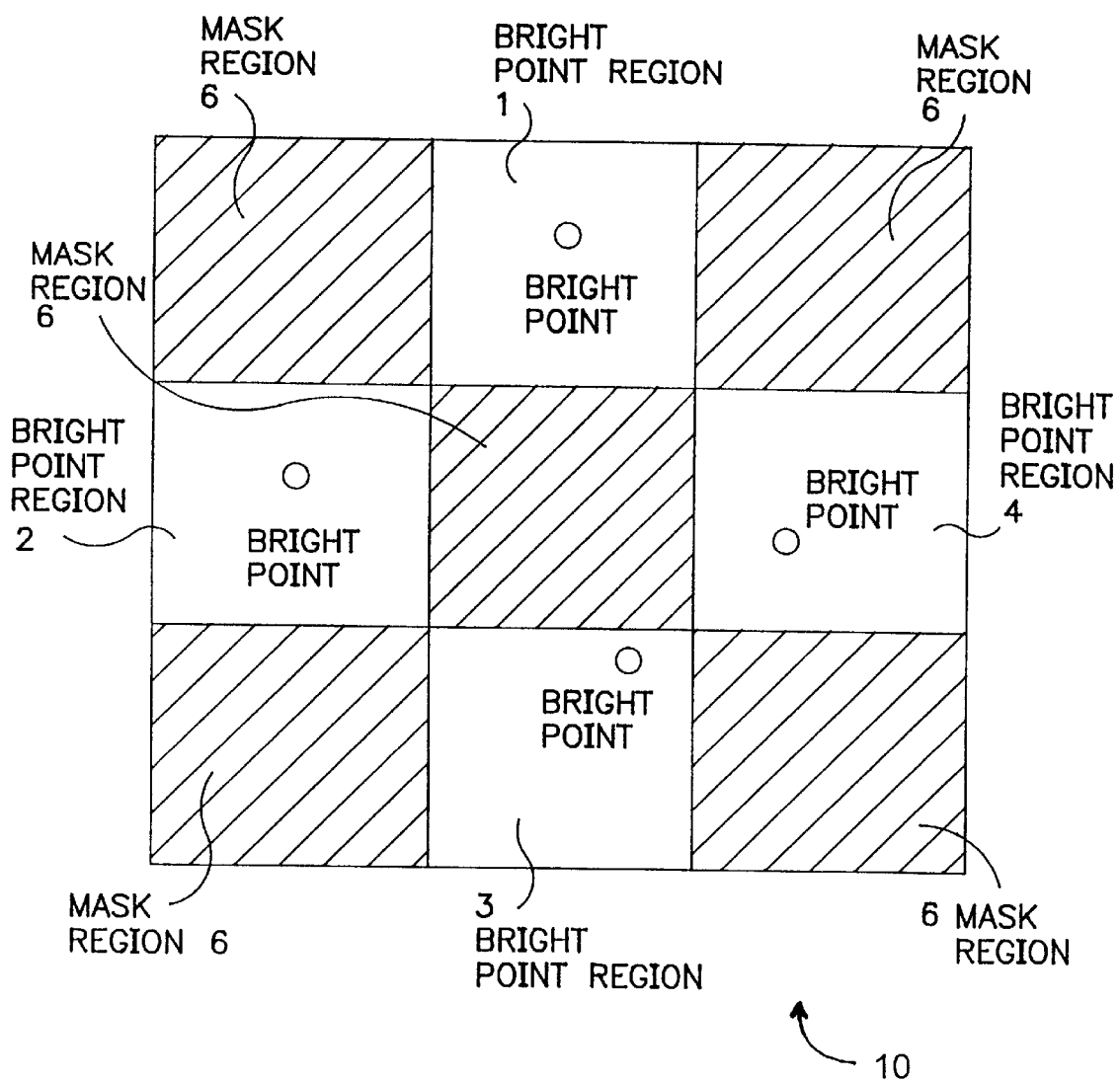
FIG. 4 is a schematic diagram of a frame memory of an ophthalmologic device according to a second preferred embodiment of the present invention.

Frame memory 10, illustrated as a second preferred embodiment in FIG. 4, includes two kinds of regions: bright point regions 1–4 and mask regions 6. However, the number of bright point regions is not limited to four. This ophthalmologic device measures corneal curvature and ocular refractive power of a subject eye. However, a similar embodiment may be applied to an ophthalmologic device which only performs measurement of the corneal curvature of a subject eye.

As described above, while measuring the corneal curvature of a subject eye, it is possible to obtain correct measurement results even in a case in which unnecessary light illuminates the eye. Even if a predetermined pattern is projected into the fundus of the eye in order to measure ocular refractive power, the predetermined pattern is unnecessary light for measurement of the corneal curvature. However, through operation of the ophthalmologic device of the present embodiments of the invention, while measuring the corneal curvature of the eye, even in the case that a predetermined pattern is projected into the fundus of the eye, it is possible to obtain correct measurement results. Thus, the present embodiments of the invention can measure corneal curvature and ocular refractive power of a subject eye simultaneously.

Although a few preferred embodiments of the present invention have been shown and described, it will be appreciated by those skilled in the art that changes may be made in these embodiments without departing from the principles and spirit of the invention, the scope of which is defined in the claims and their equivalents.

What is claimed is:

1. An ophthalmologic device to determine corneal curvature of an eye by creating a plurality of bright points on the eye from a corresponding plurality of light rays, said ophthalmologic device comprising:

an imaging unit to produce picture data corresponding to the bright points of the eye;

a frame memory to store the picture data produced by said imaging unit;

a memory controller to classify said frame memory into bright point regions in which bright points exist one at a time and mask regions in which bright points do not exist; and a control unit to calculate corneal curvature of the eye from the image data stored in the bright point regions of said frame memory.

2. The ophthalmologic device according to claim 1, further comprising:

a light source to project a predetermined pattern onto the eye and thereby produce a corresponding reflected image; and a light receiving element to receive the reflected image from the eye, wherein the picture data produced by said imaging unit includes the reflected image received by said light receiving element.

3. The ophthalmologic device according to claim 2, wherein the bright point regions are defined from a corneal configuration of the eye and a position of said light source.

4. The ophthalmologic device according to claim 2, further comprising:

a magnitude comparator to compare the picture data stored in said frame memory with a predetermined threshold value; and an area memory to store the picture data compared by said magnitude comparator which exceeds the threshold value.

5. The ophthalmologic device according to claim 1, further comprising:

a magnitude comparator to compare the picture data stored in said frame memory with a predetermined threshold value; and an area memory to store the picture data compared by said magnitude comparator which exceeds the threshold value.

6. The ophthalmologic device according to claim 1, wherein said imaging unit is a video camera.

7. The ophthalmologic device according to claim 6, wherein the video camera outputs a sync signal, said device further comprising:

an address generator to determine a storage address of the picture data in said frame memory in response to the sync signal output by the video camera.

8. The ophthalmologic device according to claim 1, wherein said control unit determines an upper, lower, left and right nominal average curvature of the cornea of the eye from the image data stored in the bright point regions of said frame memory.

9. The ophthalmologic device according to claim 1, further comprising:

an address controller to extract addresses in said frame memory of the bright point regions; and a region information memory to store the addresses extracted by said address controller.

10. An ophthalmologic device to determine corneal curvature of an eye by creating a plurality of bright points on the eye from a corresponding plurality of light rays, said ophthalmologic device comprising:

a light source to project a predetermined pattern onto the eye and thereby produce a corresponding reflected image of the predetermined pattern;

an imaging unit to produce picture data including data corresponding to the bright points of the eye and data corresponding to the reflected image;

a frame memory to store the picture data produced by said imaging unit;

a memory controller to classify said frame memory into bright point regions, a corneal reflected image region and mask regions; and a control unit to determine corneal curvature of the eye from the picture data stored in the bright point regions of said frame memory and to determine ocular refractive power of the eye from the picture data stored in said corneal reflected image region of said frame memory.

11. The ophthalmologic device according to claim 10, wherein said control unit determines an upper, lower, left and right nominal average curvature of the cornea of the eye from the image data stored in the bright point regions of said frame memory.

12. The ophthalmologic device according to claim 10, further comprising:

an address controller to extract addresses in said frame memory of the bright point regions; and a region information memory to store the addresses extracted by said address controller.

13. The ophthalmologic device according to claim 10, wherein the bright point regions are defined from a corneal configuration of the eye and a direction of the plurality of light rays.

14. The ophthalmologic device according to claim 10, further comprising:

a magnitude comparator to compare the picture data stored in said frame memory with a predetermined threshold value; and an area memory to store the picture data compared by said magnitude comparator which exceeds the threshold value.

15. The ophthalmologic device according to claim 10, wherein the plurality of light rays producing the corresponding plurality of bright points on the eye are produced from a corresponding plurality of second light sources.

16. The ophthalmologic device according to claim 10, wherein said imaging unit is a video camera.

17. The ophthalmologic device according to claim 16, wherein the video camera out puts a sync signal, said device further comprising:

an address generator to determine a storage address of the picture data in said frame memory in response to the sync signal output by the video camera.

18. An ophthalmologic device, comprising:

a first light source to create a plurality of bright points on the eye from a corresponding plurality of light rays;

a second light source to project a predetermined pattern onto the eye and thereby produce a corresponding reflected image of the predetermined pattern;

an imaging unit to produce picture data including data corresponding to the bright points of the eye and data corresponding to the reflected image;

a frame memory to store the picture data produced by said imaging unit;

a memory controller to classify said frame memory into bright point regions, a corneal reflected image region and mask regions;

a magnitude comparator to compare the picture data stored in said frame memory with a predetermined threshold value;

an area memory to store the picture data compared by said magnitude comparator which exceeds the threshold value and which is stored in frame memory in the bright point regions or stored in said corneal reflected image region; and a control unit to determine corneal curvature of the eye and ocular refractive power of the eye from the picture data stored in said frame memory.

19. The ophthalmologic device according to claim 18, wherein said imaging unit is a video camera.

20. The ophthalmologic device according to claim 19, wherein the video camera outputs a sync signal, said device further comprising:

an address generator to determine a storage address of the picture data in said frame memory in response to the sync signal output by the video camera.

* * * * *

UNITED STATES PATENT AND TRADEMARK OFFICE
CERTIFICATE OF CORRECTION

PATENT NO.: 5,815,240
DATED : September 29, 1998
INVENTOR(S): Yoichi IKI

It is certified that error appears in the above-identified patent and that said Letters Patent is hereby corrected as shown below:

Column 12, line 24, (claim 17), change "out puts" to --outputs--.

Signed and Sealed this

Twenty-third Day of February, 1999

Attest:

Q. TODD DICKINSON

Attesting Officer     Acting Commissioner of Patents and Trademarks